United States Patent [19]

Misenheimer

[11] Patent Number: 4,503,704
[45] Date of Patent: Mar. 12, 1985

[54] CARD WEB STRENGTH TEST

[75] Inventor: James R. Misenheimer, Charlotte, N.C.

[73] Assignee: Celanese Corporation, New York, N.Y.

[21] Appl. No.: 490,650

[22] Filed: May 2, 1983

[51] Int. Cl.³ .............................................. G01L 5/04
[52] U.S. Cl. ........................................ 73/159; 73/788
[58] Field of Search .................... 73/159, 37, 840, 788

[56] References Cited

U.S. PATENT DOCUMENTS 3,580,050  5/1969  Waldron ........................... 73/840 X

FOREIGN PATENT DOCUMENTS 228908  7/1925  United Kingdom .................. 73/840

Primary Examiner—Jerry W. Myracle
Attorney, Agent, or Firm—Robert J. Blanke

[57] ABSTRACT

There is disclosed an object test procedure and apparatus for measuring web strength during carding. The test method determines the amount of air flow, transverse to the web, required to break a portion of the web under inline dynamic carding conditions. The test has utility in monitoring borderline conditions in production carding processes and as a research tool for evaluating proposed variants of man-made staple fibers.

5 Claims, 9 Drawing Figures

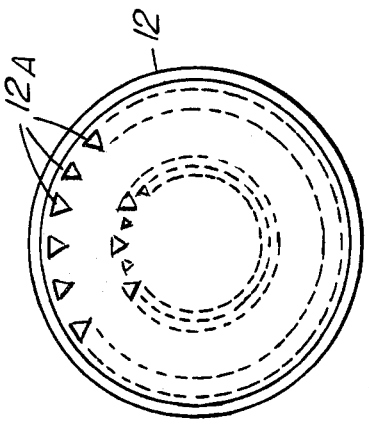
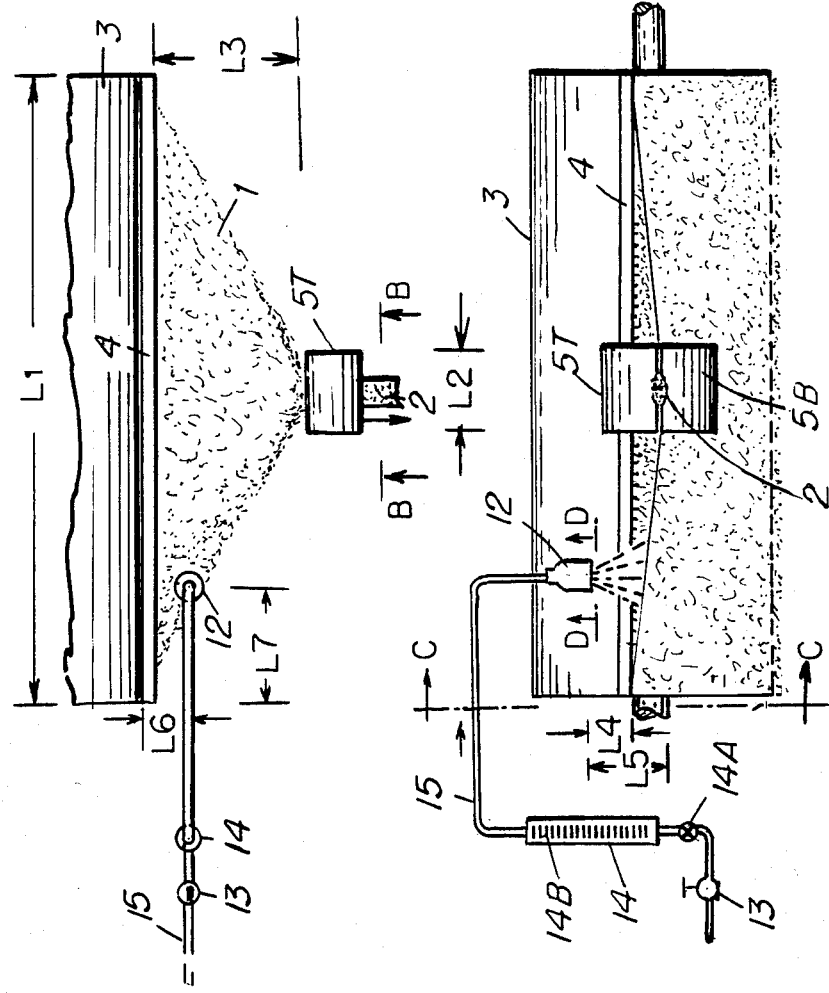
FIGURE 1D
FIGURE 1A
FIGURE 1C
FIGURE 1B

CARD WEB STRENGTH TEST

BACKGROUND

1. Field of Invention

This invention relates generally to tests for determining the suitability of staple fiber for use in textile processing operations. More particularly, it relates to a card web strength test that has utility both as a research tool and as an early warning system for production purposes.

2. Prior Art

Carding machines for converting staple fiber into carded webs are extremely old in the art. Generally, the carded web is immediately converged and partially drafted to form a sliver. Thereafter it is conventionally converted into spun yarn.

Likewise, it has been known for a very long time that the strength of the carded web significantly affects both downstream processability and the properties of the products obtained. Obviously, when the strength of part of the web falls below the forces imposed upon that portion of the web, a hole appears therein. Further, borderline conditions resulting in low strength in part of the web can lead to variability in the subsequent product of properties such as neps, imperfections, weight per yard, tenacity, elongation, and evenness.

There is no existing ASTM test for measuring the strength of a carded web. At best, there have been only subjective and/or indirect tests such as those discussed briefly below.

The "Maximum Web Draft Ratio" test is obvious from its name. Such test cannot be used on a production plant to continuously monitor the production product.

The "Sliver Shake Test Rating" is a coarse subjective test that is relatively insensitive to threshold weakening of the web which generally takes place preferentially at the edges of the web. Observed results depend to some extent upon the weight of the web.

The "Blow" test is a test that has been used for many years, in which the operator blows on the edge of the web and observes whether there is a tendency for the web to fall apart. It is crudely subjective and the observed results depend upon the weight of the web.

"Sliver Cohesion" is another test that has been used, with the test results being expressed in grams/grain/yard. It is performed by measuring the force required to draft a sliver a specified amount between two sets of rolls. A Custom Scientific CS 83 Tester or similar device can be used. However, such test results have tended to show lack of close correlation with staple properties and textile processing performance, particularly at the carding process.

SUMMARY OF THE INVENTION

In contrast to the forementioned prior art there has now been discovered an objective test method and apparatus for measuring card web strength.

Broadly, the test involves (i) blowing metered air under defined conditions through a portion of the web as it leaves the card's doffer cylinder prior to being converged into sliver form by the delivery rolls; (ii) gradually increasing the air flow, thereby initially deforming the web and finally rupturing the web; and (iii) measuring the rate of air flow when rupture occurs.

THE DRAWINGS

FIG. 1A is a semi-schematic partial plan view of a card web leaving a carding machine and being tested according to one embodiment of the invention.

FIG. 1B is a semi-schematic front elevation cross-section view of the process of FIG. 1A in the direction B—B.

FIG. 1C is a semi-schematic partial side elevation cross-section view of FIG. 1B in the direction C—C.

FIG. 1D is a ceiling view of the air spray head shown in FIG. 1B, in the direction D—D.

DESCRIPTION OF THE PREFERRED EMBODIMENTS

Figure 2:
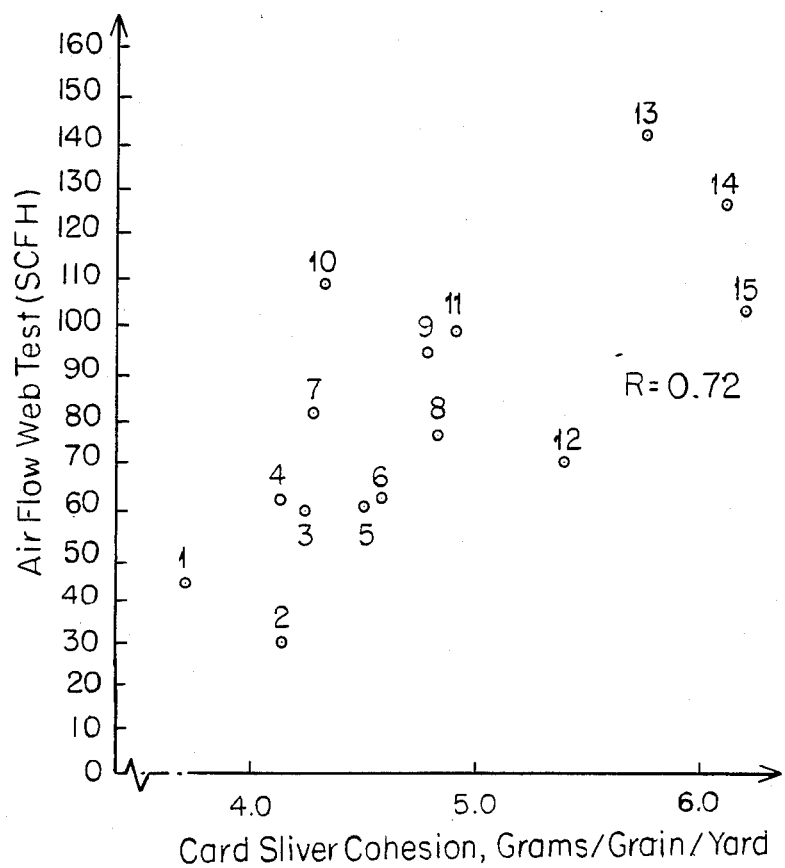
FIGS. 2-4 are graphs correlating the test of the invention with "card sliver cohesion test" for various categories of carded web.

The nature of the preferred embodiments of the invention is best understood by the Examples hereinafter. The invention is not limited to the Examples.

EXAMPLES 1-15

In summary, fifteen carded webs were separately and conventionally prepared from fifteen different samples of polyester staple fiber. In addition, the test of the invention was used in-line on the carded web simultaneously while the web was being drafted and converged into sliver form as shown in FIGS. 1A-1D. The results from the test of the invention were correlated with several prior art tests as shown in FIGS. 2-6, and various conclusions drawn therefrom, as described below.

All of the carded webs were formed from the different samples of staple fiber under similar processing conditions, by means of a standard Saco Lowell Cotton Card, followed by standard calendar rolls to withdraw and converge the carded web. FIGS. 1A-1D illustrate the process between and including, firstly, the point where the card web leaves the card web-doffer cylinder and, secondly, the point where the sliver emerges from the calendar rolls. FIG. 1A shows in plan view the conventional card web (1); sliver (2); card doffer cylinder (3); doffer comb (4); and the top roll (5T) of a pair of calendar rolls (5B and 5T). FIG. 1B shows the same features in front elevation. FIG. 1C shows the same features in side elevation.

FIGS. 1A-1C also illustrate the test of the invention in progress. Thus, FIG. 1B shows air (11) being sprayed downwardly on to the web from an air spray head (12). The air is supplied to the air spray head at a controlled and measured rate by means of air being fed through a pressure regulator (13) from a source of pressurized air (not shown). The air then passes through a Dwyer air flow meter (14) having a needle valve (14A) to adjust air flow and an indicator (14B) that indicates the amount of air flow over a range of 20 to 200 SCFH, before passing through plastic pipe (15) to the air spray head.

FIG. 1D is an enlarged ceiling view of the air spray head in the direction D—D of FIG. 1B. The air spray head was a standard Sears Model 2004 "Water Saver" home shower head. It had 70 triangular-shaped orifices (12A) arranged in two concentric circles having diameters of ⅜ and 1¼ inches. The outer circle of holes contained 40 triangular holes spaced 3/32 inches apart. Base and height of each triangle was approximately 1/32 of an inch. The inner circle of holes consisted of two sizes of triangular holes arranged in alternating sequence. There were 15 larger slots each 1/32 of an inch high by 1/32 of an inch wide and 15 smaller slots each 1/64 of an inch high by 1/64 of an inch wide. The holes were spaced at 3/32 of an inch.

The values of the dimensions shown as L1-L7 in the Figures were as follows: L1, doffer cylinder length, 41 inches; L2, calendar rolls length, 6 inches; L3, web length from doffer comb to calendar rolls, 12 inches; L4, distance from air spray head to web, 2 inches; L5, vertical distance from air spray head to the nip of the calendar rolls, 4¼ inches; L6, distance of air spray head from doffer comb, 2¼ inches; and L7, distance of air spray head from one end of the doffer cylinder, 7 inches.

It should be noted that, prior to these Examples, preliminary trials had been conducted with several types of air dispersing heads and at various positions of the air dispersing head relative to the web. These preliminary trials had led to the selection of the specific Sears Model 2004 "Water Saver" and to the selection of the position of the air dispersing head. In particular, the edge of the web closest to the card comb was found to be the most critical zone in which to mount the air blowing device.

In each of Examples 1-15, the staple-web-sliver process shown in FIGS. 1A-1C was initially set up to give a standard carding test at 60 grain sliver delivery. Once these standard processing conditions had been established, the following air flow web strength test was performed. The air pressure regulator 13 of FIG. 1B, was opened from 0 psig to 30 psig. Needle valve 14A of FIG. 1B was then gradually and cautiously opened in stepwise manner. During this operation the portion of the web subject to the air flow was constantly observed. In general, the web became deformed as the air flow was increased and then, with further increase in air flow, suddenly separated in the form of a split. Whereupon; the airflow registered by indicator 14B was noted and the needle valve closed. Once the web had stabilized again, the needle valve was again opened and a further measurement made of the critical air flow rate. Five such readings were made on each type of web and the results averaged. The range for the five tests was typically narrow and about 5 to 10 SCFH.

Fifteen different samples of polyester staple fiber were processed and tested in the foregoing manner. Some of the samples of staple were commercially available; others were only experimental. All of the samples had uniform staple length of about 1½ inches, and average d.p.f. of about 1.5. The samples differed from each other with respect to properties such as crimp characteristics (such as percent crimp, cpi and crimp stability) and the fiber finish (type and amount) on the fibers.

Further, slivers were made at web draft ratios of 1.0 during each of the foregoing trials. The slivers were collected and tested for card sliver cohesion using the Custom Scientific Model 83 at 1.78 draft ratio and feed to delivery roll spacing of 1.75 inches.

Figure 3:
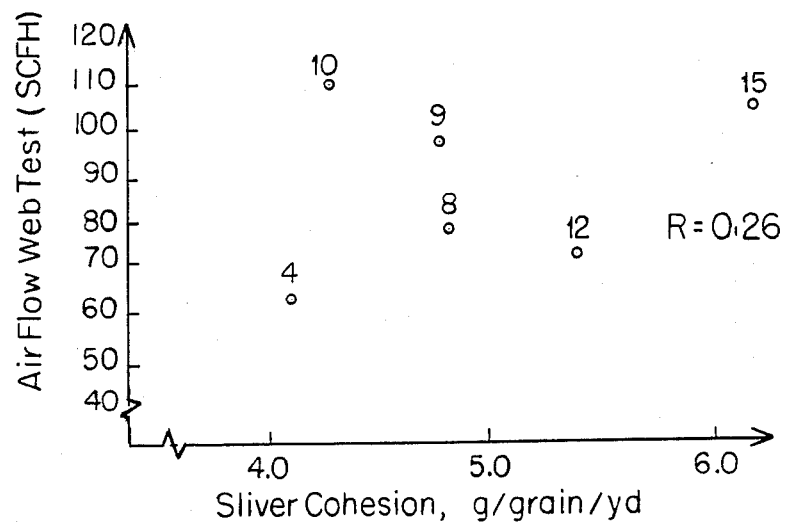
Figure 4:
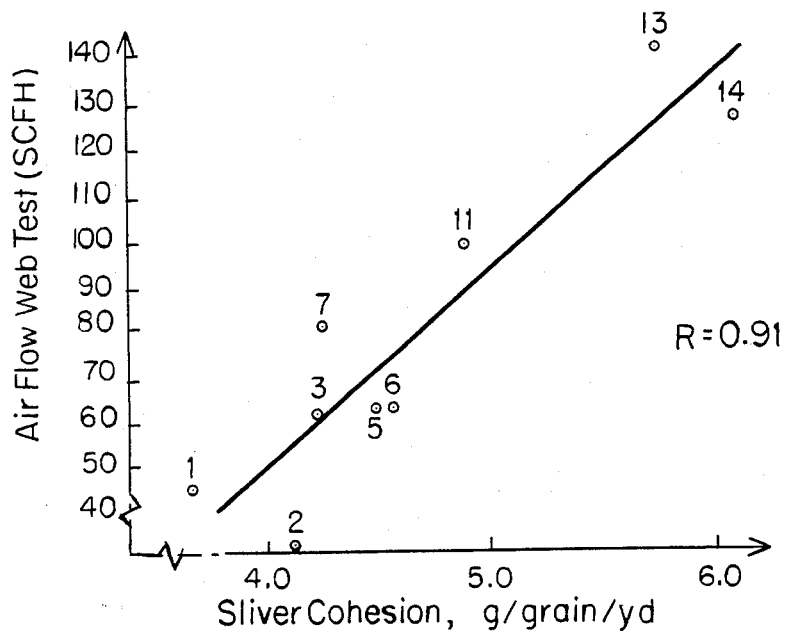

FIG. 2 is a plot of corresponding pairs of test data for the air flow web test and the sliver cohesion test, for each of the fifteen samples. It will be noted that the coefficient of correlation, R, of the air test results and sliver cohesion results was not especially high (R=0.72). However, interesting results were noted when the data in FIG. 2 was separated into FIG. 4 (which relates to nine samples that had very similar fiber finish properties) and FIG. 3 (which relates to the remaining six samples that had widely different fiber finish properties). Thus, FIG. 4 shows an R value of 0.91, whereas FIG. 3 shows an R value of only 0.26. These results suggest that finish is the dominant but probably not the only fiber factor in sliver cohesion. Web strength appears to be controlled by crimp and other non-finish staple characteristics.

Figure 5:
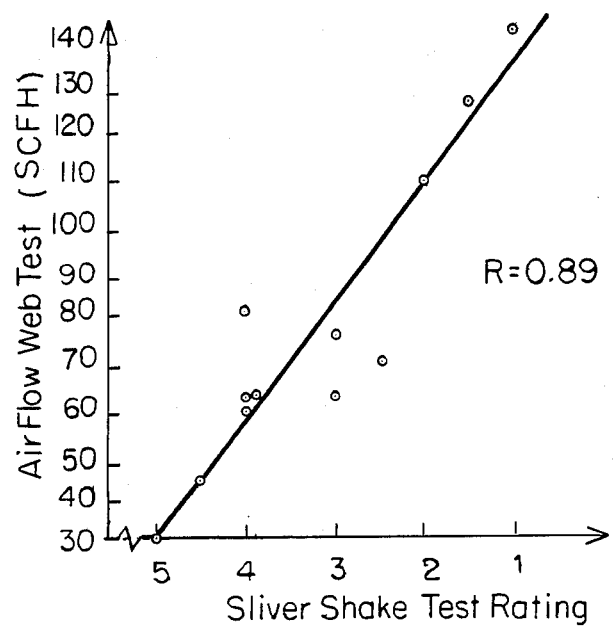
FIG. 5 is a graph correlating the test of the invention with the "sliver shake test rating".
Figure 6:
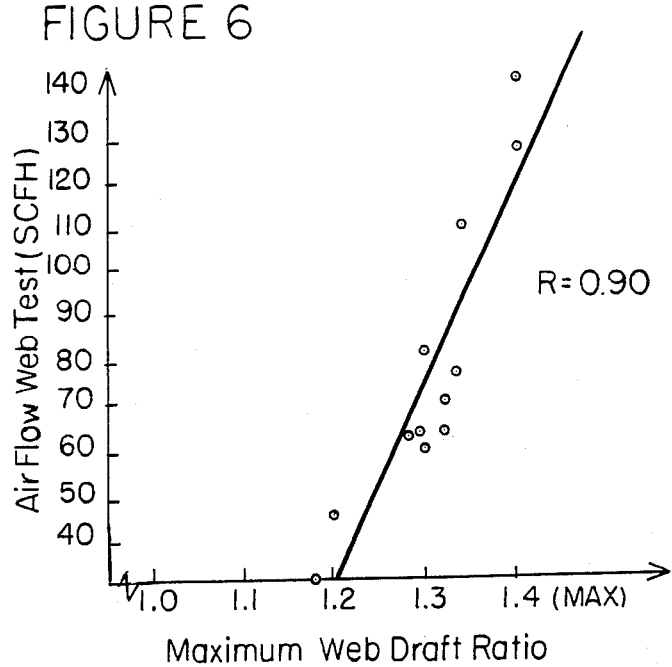
FIG. 6 is a graph correlating the test of the invention with the "maximum web draft ratio test".

In addition to the foregoing tests, webs formed from each of the fifteen samples were tested by the forementioned subjective "shake test" and by the "web draft ratio test" using variable speed calendar rolls. Correlation of results from the air flow web test was good with both the "shake test" (R=0.89) and web draft ratio test (R=0.90) as indicated in FIGS. 5 and 6, respectively. Thus, the air flow test is a good objective replacement for the subjective method now typically used to judge web strength by shaking a section of card web until it falls apart.

What I claim is:

1. A method for objectively measuring the strength of a web comprising staple fibers, which comprises the steps of:
   (i) passing air at an increasing rate of flow through a portion of a carded web downstream of a carding machine's doffer cylinder and upstream of means for withdrawing said carded web, thereby initially deforming the carded web and eventually rupturing the carded web; and
   (ii) measuring the passed air's flow rate required to rupture the carded web.

2. The method of claim 1 which comprises converging the carded web into a sliver, and blowing air through a portion of the web located at a distance of up to about 12 inches from an edge of the converging web.

3. The method of claim 2 which comprises spraying air at spray-exit velocities of up to 15,000 feet/minute in a direction perpendicular to the web.

4. The method of claim 2 which comprises spraying air at a rate of up to 200 SCFH.

5. The method of claim 2 which comprises locating air blowing means at a distance from the web within the range one to ten inches.

* * * * *